(12) United States Patent
Wilber et al.

(10) Patent No.: US 6,623,756 B1
(45) Date of Patent: Sep. 23, 2003

(54) DIRECTLY COMPRESSED SOLID DOSAGE ARTICLES

(75) Inventors: William R. Wilber, Avon Lake, OH (US); Jian-Hwa Guo, Hudson, OH (US); Edward S. Greenberg, Solon, OH (US)

(73) Assignee: Noveon IP Holdings Corp., Cleveland, OH (US)

( * ) Notice: Subject to any disclaimer, the term of this patent is extended or adjusted under 35 U.S.C. 154(b) by 0 days.

(21) Appl. No.: 09/559,687

(22) Filed: Apr. 27, 2000

(51) Int. Cl.[7] .............................. A61K 9/20; A61K 9/26; A61K 9/14
(52) U.S. Cl. ....................... 424/465; 424/464; 424/469; 424/470; 424/489
(58) Field of Search .............................. 424/464, 465, 424/469, 470, 489

(56) References Cited

U.S. PATENT DOCUMENTS

| | | | | | |
|---|---|---|---|---|---|
| 2,798,053 A | * | 7/1957 | Brown | .................. | 260/2.2 |
| 3,915,921 A | * | 10/1975 | Schlatzer, Jr. | .............. | 260/17.4 |
| 4,267,103 A | * | 5/1981 | Cohen | .................. | 260/17.4 |
| 4,952,651 A | * | 8/1990 | Kasai et al. | ................ | 526/201 |
| 5,288,814 A | * | 2/1994 | Long, II et al. | ............ | 525/450 |
| 5,780,055 A | * | 7/1998 | Habib et al. | ................ | 424/464 |
| 5,858,406 A | | 1/1999 | Stead et al. | | |

FOREIGN PATENT DOCUMENTS

WO    WO 93/23457    * 11/1993

OTHER PUBLICATIONS

Bulletin 17: Controlled Release tablets and Capsules; copyright 1996 the BFGoodrich Company, Pharmaceuticals Division.

* cited by examiner

Primary Examiner—Thurman K. Page
Assistant Examiner—S. Tran
(74) Attorney, Agent, or Firm—Thoburn T. Dunlap; Hudak, Shunk & Farine Co. LPA

(57) ABSTRACT

Solid dosage articles such as pharmaceutical tablets for the controlled release of a desired compound such as an active ingredient are directly compressed from a flowable, compressible mixture of the active ingredient, a slightly crosslinked rheology modifying polymer or copolymer, and one or more excipients. The rheology modifying polymer or copolymer is a granulated powder of suitable particle size and is generally made from one or more unsaturated (di) carboxylic acids, half ester thereof, and other optional monomers.

14 Claims, 1 Drawing Sheet

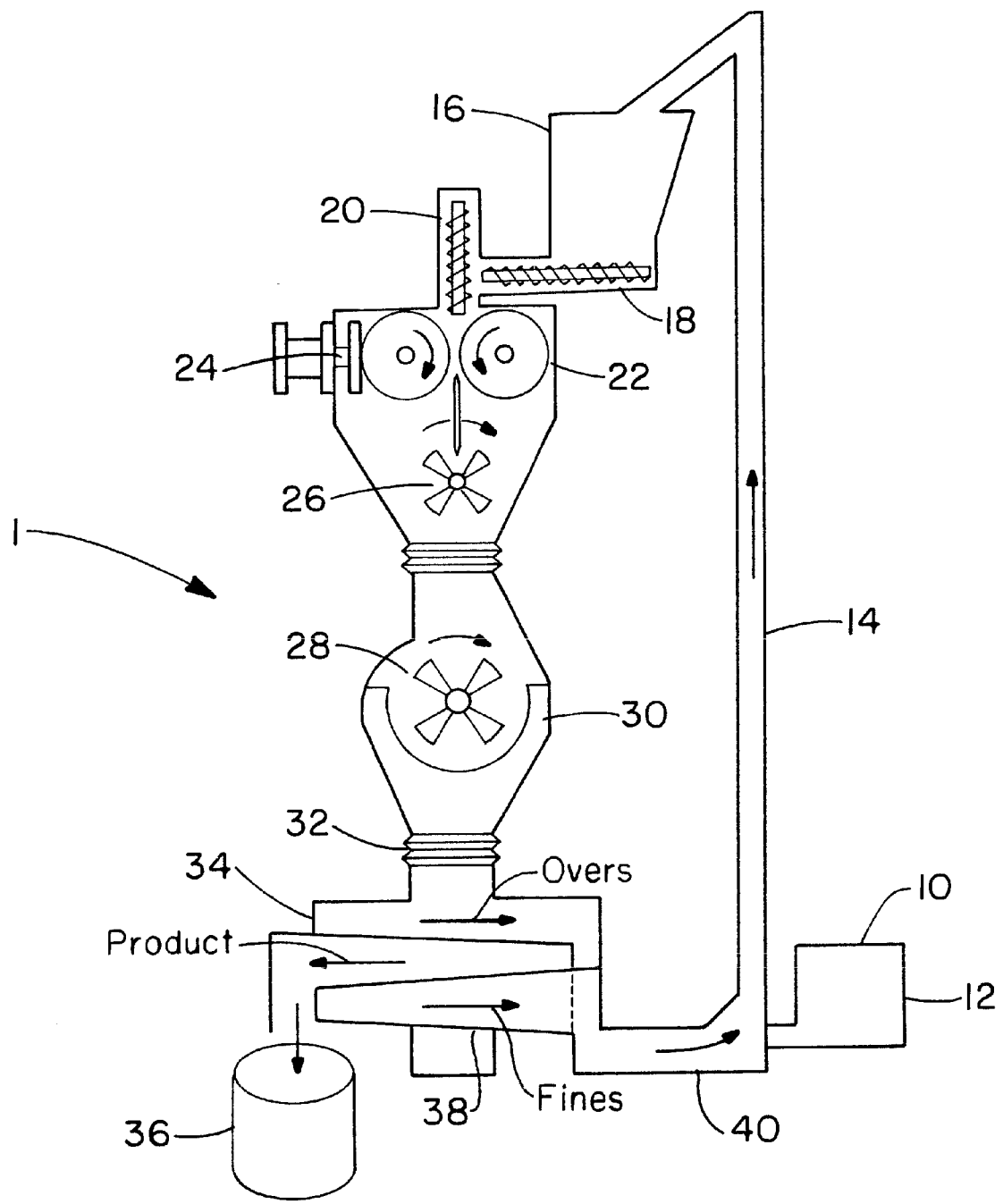

DIRECTLY COMPRESSED SOLID DOSAGE ARTICLES

FIELD OF INVENTION

The present invention relates to slightly cross-linked polymers and copolymers generally derived from one or more unsaturated carboxylic acids, which are mixed with one or more active ingredients, and one or more excipients, wherein the mixture has desired properties such as good flow rates and appropriate compressibility so that without further processing it can flow through a die and be directly compressed into a tablet or other solid dosage article.

BACKGROUND OF THE INVENTION

Heretofore, rheology agents were generally unsuitable for utilization in the formation of directly compressed tablets generally due to their fine particle size, static generating nature, and poor flow characteristics which they imparted to powder mixtures such as pharmaceutical mixtures. In order to form such powder mixtures, a rheologic agent in the form of a non-granulated powder was mixed with an active ingredient and an excipient and granulated. Subsequently, the granulated mixture was compressed into a tablet. The rheologic agents utilized included compounds such as Carbopol® 934 PNF, 971 PNF, 974 PNF, 940, 941, and 934 made by B.F. Goodrich Company. Other similar rheologic agents include Synthalen K, L, and M made by 3V/Sigma, Hivis Wako made by Wako Pure Chemicals Co., and Aqupec made by Sumitomo Seika.

SUMMARY OF INVENTION

Solid dosage forms such as tablets for pharmaceutical uses are directly compressed from a mixture of granular rheology modifying polymers or copolymers, active ingredients, and excipients. The rheology modifier is a homopolymer or copolymer derived from one or more unsaturated carboxylic acids and is slightly cross-linked. The rheology modifying polymer or copolymer is processed into a desirable granular size as by being compacted into large agglomerates or aggregates and subsequently fractured into smaller granules and generally screened to obtain suitable particle sizes which have low amounts of dust. The polymer or copolymer becomes highly swollen in an aqueous medium and is suitable for use in a human being or animal. The polymer or copolymer can be combined with numerous different types of active ingredients for one or more specific end uses. Moreover, numerous different types of excipients can be utilized. The combination of the one or more excipients, active ingredients, and the rheology modifying polymer or copolymer when mixed generally form suitable mixtures for directly compressible tablets because of their good flow characteristics and compressibility.

DESCRIPTION OF THE DRAWINGS

The FIGURE is a schematic of a compaction/granulation apparatus.

DETAILED DESCRIPTION OF THE INVENTION

The polymeric rheology modifier provides controlled release of biologically active compounds as contained in a tablet so that when placed in water, the modifier of the invention swells to form a viscous gel which retards diffusion of the active material. The rheology modifying polymers or copolymers are derived from one or more unsaturated carboxylic acid monomers generally having one or two carboxylic acid groups, desirably having one carbon to carbon double bond and containing generally a total of from 3 to about 10 carbon atoms and preferably from 3 to about carbon atoms such as α-β-unsaturated monocarboxylic acids, for example, acrylic acid, methacrylic acid, and crotonic acid, and the like, or dicarboxylic acids such as itaconic acid, fumaric acid, maleic acid, aconitic acid, and the like. Moreover, half ester monomers of such diacids with alkanols containing from 1 to about 4 carbon atoms can also be utilized. Preferred acids include acrylic acid or maleic acid.

Optionally, one or more oxygen containing unsaturated comonomers having a total of from 3 to about 40 carbon atoms, such as esters of the above unsaturated (di)carboxylic acids, that is mono or di, especially alkyl esters containing a total of from 1 to about 30 carbon atoms in the alkyl group can also be utilized as comonomers to form the copolymer. Examples of such esters include ethyl acrylate, butyl acrylate, 2-ethylhexyl acrylate, dodecyl acrylate, hexadecyl acrylate, and octadecyl acrylate, and the like, with the $C_{10}$ to $C_{30}$ acrylates being preferred.

Another optional class of comonomers are the various anhydrides of the above noted carboxylic acids such as maleic anhydride, and the like. Moreover, another optional class of suitable comonomers are the various alkyl vinyl ethers wherein the alkyl group contains from 1 to about 20 carbon atoms with examples including ethyl vinyl ether, methyl vinyl ether, and the like.

The amount of the one or more oxygen containing acid comonomers when utilized is generally a minor amount, such as from about 0.01% to about 40% by weight, desirably from about 0.5% to about 35% by weight, and preferably from about 1% to about 25% by weight based upon the total weight of all the rheology modifying polymer or copolymer forming monomers and comonomers. Thus, the amount of the one or more unsaturated carboxylic acid monomers, half esters thereof, or combinations thereof, is generally from about 60% to 99.99% by weight, desirably from about 65% to about 99.5% by weight, and preferably from about 75% to about 99% by weight based upon the total weight of all rheology modifying polymer or copolymer forming monomers or comonomers.

The various rheology modifying polymers or copolymers of the present invention are generally anhydrous. That is, they generally contain 5 parts by weight or less, desirably 3 parts or 2 parts by weight or less, and preferably 1 part or less by weight, and even nil, that is no parts by weight, of water per 100 parts by weight of the one or more rheology modifying polymers or copolymers.

The one or more rheology modifying polymers or copolymers also generally contain low amounts by weight of multivalent metal cations such as iron, for example 1 part by weight or less, desirably 0.1 part by weight or less, and preferably 0.01 part by weight or less per 100 parts by weight of all rheology modifying polymers or copolymers. The rheology modifying polymers or copolymers can contain up to five parts by weight of monovalent metal cations such as sodium, potassium, and the like.

It is an important aspect of the present invention that the rheology modifying polymer or copolymer be slightly cross-linked with one or more polyunsaturated monomers or comonomers. Suitable cross-linking agents generally include the various allyl ethers of sucrose or pentaerythritol, or derivatives thereof, or various polyalcohols. Specific examples include; diallylphthalate, divinyl benzene, allyl (meth)acrylate, ethylene glycol di(meth)acrylate, divinylglycol methylene bisacrylamide, trimethylolpropane tri (meth)acrylate, diallyl itaconate, diallyl fumarate, or diallyl maleate. Derivatives of castor oils or polyols such as esterfied with an ethylenically unsaturated carboxylic acid and the like can also be used. Preferred cross-linking agents include allyl ether of sucrose, allyl ether of pentaerythritol, diallylphthalate, and combinations thereof.

The amount of the cross-linking agent is from about 0.01 to about 2 parts by weight, desirably from about 0.02 to about 1.5 parts by. weight, and preferably from about 0.03 to about 1 part by weight per 100 total parts by weight of the one or more monomers or comonomers. Slightly cross-linked rheology modifying polymers or copolymers are utilized in as much as they can conform under light pressure as in a compacting apparatus and in a mill to form granular mixtures which readily flow. Highly cross-linked rheology modifying polymers or copolymers tend to not conform under light pressure and consequently fracture in a mill thus forming fine sized particles which do not readily flow and are therefore unsuitable for forming a directly compressed solid dosage form. Such moderate to highly cross-linked polymers or copolymers also tend to generate fisheyes therein. That is, when placed in water, they exhibit incompletely swollen particles easily visible in the transparent gel.

Examples of suitable slightly cross-linked commercially available rheology modifying polymers or copolymers include Carbopol®, 941, 971 PNF and 981 manufactured by B.F. Goodrich, as well as Synthalen L made by 3V/Sigma, Aqupec HV-501 and HV 501E made by Sumitomo Seika.

The polymers or copolymers of the present invention are produced by conventional methods known to the art and to the literature such as by dispersion or precipitation polymerization utilizing suitable organic solvents such as various hydrocarbons, esters, halogenated hydrocarbon compounds and the like, with specific examples including aromatic solvents such as benzene, or toluene; various cycloaliphatic solvents such as cyclohexane; various esters such as ethyl acetate and methyl formate, ethyl formate; various chlorinated hydrocarbons such as dichloromethane; and combinations thereof. Preferred solvents generally include benzene, methylene chloride; blends of ethyl acetate and cyclohexane, or ethyl acetate, and the like.

The one or more monomers or comonomers are polymerized in a manner known to the art and to the literature such as described in U.S. Pat. Nos. 2,798,053; 3,915,921; 4,267,103; 5,288,814; and 5,349,030 which are hereby fully incorporated by reference. Desirably, the rheology modifying polymers or copolymers have an acidic pH in water as from about 2.0 to about 4.0, desirably from about 2.5 to about 3.5.

It is also an important aspect of the present invention to granulate the slightly cross-linked rheology modifying polymers or copolymers. The same can be accomplished by processes known to the art and to the literature such as for example by roller compaction, by slugging, or utilizing wet methods such as a fluidized bed.

A desired method for granulation is set forth in the drawing. A granulator, generally indicated by the numeral 1, contains a feeder 10 which feeds the slightly cross-linked rheology modifying polymer and copolymer to the bottom of hopper 12. The polymer or copolymer is then fed through feed channel 14 to upper hopper 16. Hopper 16 additionally contains oversized and/or fine sized granulated polymers or copolymers which are not of a suitable size as set forth herein below. The slightly cross-linked polymer or copolymer in hopper 16, along with the oversized and/or fine sized granulated polymers or copolymers, is then fed via horizontal feed screw 18 to the granulator. The rate of rotation of horizontal feed screw 18 can be adjusted to permit continuous flow of the various sized polymers or copolymers into the granulator without clogging. Then, vertical screw 20 compresses and deaerates the various sized polymers or copolymers fed thereto and feeds the same into compaction rollers 22. Hydraulic actuator 24 applies a suitable pressure to the compaction rollers.

Pressure is applied to the compaction rollers via the hydraulic actuator or other compaction device to produce a compacted material having a density of about 0.3 g/cc to about 1.5 g/cc. Preferably, the density of the compacted material is from about 0.38 g/cc to about 0.5 g/cc. These densities form strong enough aggregates and/or agglomerates such that the amount of undersized particles can be reduced without removing so much of the voids, cracks, and crevices (void volume) within the aggregates and agglomerates to prevent them from uniformly swelling in water or electrolyte solutions. The compaction rolls may have circumferential corrugations, pocket indentations or corrugations in the axial direction across the width of the roll.

Desirably, the compaction rollers rotate in opposite directions so that the various sized rheology modifiers fed thereto are pulled between the rollers, compressed, and subsequently dropped downwardly into pre-break mechanism 26. Pre-break mechanism 26 breaks the compressed various sized rheology modified chips into flakes which then fall into attritor 28. The attritor subsequently further breaks up the chips into flakes which fall through screen 30. The granulated particles then fall into screening apparatus 32 which generally contains a plurality of screens which separate out oversized as well as undersized (i.e. fines) particles. The desired sized particles are fed to product bin 36. The over and undersized particles 38 are recycled through feed mechanism 40 which directs the same into feed channel 14 thereby recycling the oversized and undersized particles to upper hopper 16. The above granulation procedure is set forth in U.S. patent application Ser. No. 09/329,471, filed Jun. 10, 1999 for 'Controlled Release Polyacrylic Acid Granules and a Process for Preparing the Same' which is hereby fully incorporated by reference.

The granulated rheology modifying polymers and copolymers desirably have a specific particle size range so that when blended with the one or more active ingredients, and one or more excipients, a flowable mixture is produced. Desirably, the particle or granular size of the one or more polymers or copolymers can be classified as falling within size ranges as defined by U.S. Standard Mesh screens. For example, the particle size of the granulated rheology modifying polymers or copolymers is generally that which falls through 40 mesh but is retained on 200 mesh, desirably that which falls through 45 mesh but is retained on 150 mesh, and preferably that which falls through 50 mesh but is retained upon a 100 mesh screen. The amount of oversized or undersized material which is contained within such ranges is also generally limited. For example, oversized material may be contained within a desired particle range as when the partides are elongated. Undersized particles, or fines, can also be found within the desired particle size range as when the same stick to or are tied up between desired particle size products. The amount of the oversized material contained within the granular particles of the above desired ranges is generally about 5 percent or less, desirably about 3 percent or less, and preferably about 1 percent or less by weight based upon the total weight of the particles falling through the larger sized mesh screen but retained on the smaller mesh screen. Similarly, the amount of fines contained within the granular particles of the above desired ranges is generally about 25 percent or less, desirably about 20 percent or less, and preferably about 15 percent by weight or less of the total particles which fall between the larger mesh screen but are retained by the smaller mesh screen. The net result is that suitable sized granules are utilized which flow freely through a die so that they can be directly compressed. As noted above, the same is not true of granular rheology modified particles made from moderate to highly cross-linked polymers or copolymers inasmuch as the same tend to fracture and form excessive amounts of fine sized particles which clog a desired diameter die, or other narrow constriction. If compressed to avoid the formation of excessive amounts of fine sized particles, the rheology modified particles tend to form fisheyes as described above, and swelling is impeded so that desirable control release properties are impaired.

The granulated slightly cross-linked rheology modifying polymers or copolymers of the present invention have several favorable properties such as thickening efficiency, bulk density, and tap density. When dispersed in water at a concentration of 10 grams per liter and neutralized to a pH of 7, the granulated polymers or copolymers generally retain at least 70, 80, and even 90 percent of the thickening capacity of the original powder. The viscosity of such a solution is desirably at least 350, 400, or 450, and preferably at least 1,400, 1,600, or 1,800 centipoise to about 16,000 centipoise.

The bulk density of the granules is measured according to a typical bulk density method for powders. A 30–100 mL cup is used which can be lightly tapped one time after filling. The powder is dropped from a powder funnel which discharges about 4 to 8 cm above the rim of the cup. The excess material which accumulates above the rim of the cup can be removed by scraping with a spatula and the weight of the contents determined. The bulk density is the weight of the contents divided by their volume. Suitable bulk densities generally range from about 0.35 to about 0.60 and desirably from about 0.38 to about 0.55 grams per cubic centimeter. A tap density can also be determined using a 100 mL graduated cylinder instead of a cup. The powder is discharged from the bottom of a powder funnel as set forth above. A tap density apparatus such as a J. Englesmann A-G Tap Density Apparatus is used to tap the cylinder and contents 1,000 times. The volume and weight of the powder after tapping is recorded and the density is calculated as the weight divided by the volume. Suitable tap densities range from about 0.40 to about 0.70, desirably from about 0.42 to about 0.60 and preferably from about 0.45 to about 0.58 grams per cubic centimeter.

An important component of the directly compressed solid dosage article such as a tablet is the utilization of an active ingredient. Such active ingredient(s) are generally classified as biological ingredients such as pharmaceutical, medicinal, nutritional, and the like.

Examples of biological ingredients include Tretinoin; Progesterone; Methyl Salicylate; Capsaicin; Lidocaine; Prilocaine; Methyl Nicotinate; Crotamiton; Avobenzone; Oxybenzone; Kaolin; Pectin; Sulfamethoxazole; Fentoin; Albendazole; Pilocarpine HCl; Phenylpropanolamine HCl; Fluocinonide; Formulated Actives in the 1998 Physicians Desk Reference®, and the like.

Various classes of medicinals which can be utilized include the following: androgenotherapy; anesthetic; anorectic; anti-allergy; anti-asthmatic; antibacterial; antibiotics; anti-depressants; antidermatosis; anti-diarrhea; anti-emetics; antifungal; anti-inflammatory; anti-inflammatory analgesic; anti-inflammatory. anti-pruritics; anti-inflammatory vasoconstrictive; anti-malaria; anti-parasitic; antiseptic; antiviral; anti-vomiting; bronchitis; burns; conjunctiva, cornea therapy; cough; estrogen; gastrointestinal treatment; glaucoma; hemorrhoid treatment; hair loss; heart disease; heart-rhythm disorder; impotency; laxative; progestogen; revulsive; slimming; spasmophilia; tooth health; urology; vein therapy; wound treatment; and the like.

Various other active medicinal ingredients which can be utilized include acetazolamide; aescin; aesculi hippocastan; allantoine; amfepramone; aminopropylon; amorolfine; androstanolone; arnica; bamethan sulfate; benproperinembonate; benzalkonium chloride; benzocaine; benzoyl peroxide; benzyl nicotinate; betamethasone; betaxolol chlohydrate; buphenine hydrochloride; caffeine; calendula; camphor; cetylpyridinium chloride; chloroquin phosphate; clarithromycin; clemastinhydrogene fumarate; clindamycin-2-dihydrogene phosphate; clobetasol-propionate; clotrimazole; codeine phosphate; croconazole; crotamiton; dexamethasone acetate; dexpanthenol; diclofenac; diethylamine salicylate; diflucortolone; diflucortolone valerate; diflucortolone, chlorquinaldol; difluoroprednate; dimethyl sulfoxide; dimeticone 350-silicium dioxide; dimetinden; dimetindenmaleat; disopyramide; domperidone; ergotoxine; estradiol; estriol; etofenamate; felbinac; flubendazole; flufenamic acid; fluocinolone; flubcinolone acetonide; fluocortolone; fusidic acid; gelacturoglycani; heparine; hydrocortisone; hydroxyethyl salicylate; ibuprofen; idoxuridine; imidazole salicylate; indomethacin; isoprenaline sulfate; ketoprofen; levomenthol; lidocaine hydrochloride; lindane; menthol; mepyramine; mesalazine; methyl nicotinate; methyl salicylate; metronidazole; miconazole; minoxidil; naftifin; nalixidic acid; naproxen; niflumic acid; nifuratel; nifuratel nystatine; nifuroxazide; nitroglycerin; nonivamid; nystatinnifuratel; omoconazole nitrate; o-rutoside; oxatomide; oxerutin; oxyphenbutazone; pancreatine; pentosane polysulfate; phenolphthalein; phenylbutazone-piperazine; phenylephrine; pilocarpine; piroxicam; plant extracts; polidocanol; polycarbophil; polysaccharide; potassium phosphate; prednisolone; prilocaine; primycin sulphate lidocaine; progesterone; proteins; racem.camphor; verapamil; viloxazine; vitamin B6; xylitol; xylometazoline; zincum hyaluronicum, and the like.

Other active compounds include retacnyl tritinoine; retinol palmitate; salicylamide; salicylic acid; sobrerol; sodium alginate; sodium bicarbonate; sodium fluoride; sodium pentosan polysulfate; sodium phosphate; terpine; theophylline; thromboplastin; thymol; tocopherol acetate; tolmetin; tretinoin; troxerutine, and the like.

Various pharmaceutical ingredients which can be utilized include Ascorbic Acid; Guaifenesin; Quinidine Gluconate; Aspirin; Isosorbide Dinitrate; Quinidine Sulfatef; Atenolol; Isoniazid; Sodium Valproate; Caramiphen HCl; Lithium Carbonate; Sulfamethizole; Chlorpheniramine Maleate; Mepyramine Maleate; Theophylline; Dexchlorpheniramine; Methadone HCl; Thiamine; Diethyl Propion HCl; Metoclopramide; Tridecamine; Diphenhydramine; Nitrofurantoin; Verapamil HCl; Ephedrine HCl; Phenylpropanolamine HCl; Viloxazine; Furosemide; Pseudoephedrine; 2-Ethylhexyl Salicylate; Clocortolone pivalate; Kaolin; Permethrin; Adapalene; Crotamiton; Lidocaine; Phenylbenzimidazole Sulfonic Acid; Albendazole; Desoximetasone; Menthol; Phenylpropanolamine; Avobenzone; Dimethicone; Mesalamine; Pilocarpine HCl; Benzalkonium Chloride; Methyl Nicotinate; Piperonyl Butoxide; Benzocaine; Erythromycin; Methyl Salicylate; Prilocaine; Benzoyl Peroxide; Ethylhexyl p-Methoxycinnamate; Metronidazole; Progesterone; Betamethasone dipropionate; Fenytoin; Naftifine HCl; Pyrethrum Extract; Betaxolol HCl; Fluocinonide; Nalidixic acid; Rimexolone; Camphor; Guaifenesin; Nitrofurantoin; monohydrate; Simethicone; Capsaicins; Homosalate; Octyl Methoxycinnamate; Sulfamethoxazole; Clarithromycin; Hydrocortisone; Oxybenzone Tretinoin; Clindamycin phosphate; Hydrocortisone valerate; Padimate; Zinc Chloride; Clobetasol propionate; Hydroquinone; Pectin; 2-Ethylhexyl Salicylate; Clocortolone pivalate; Kaolin; Permethrin; Adapalene; Crotamiton; Lidocaine; Phenylbenzimidazole Sulfonic Acid; Albendazole; Desoximetasone; Menthol; Phenylpropanolamine; Avobenzone; Dimethicone; and Mesalamine.

As known to those skilled in the art and to the literature, the amount of the various active ingredients can vary widely, for example depending upon the type of end use, the biological or pharmaceutical activity of the ingredient, the desired biological pharmaceutical dose level, and the like. Thus, for example, the active ingredient can be used in an amount from a few parts per million up to approximately 80 percent by weight of the directly compressed tablet.

The excipients are generally utilized to give a desirable slow release profile as well as other desirable attributes of a compressed tablet such as color, hardness, crushing strength, and low friability, etc. Accordingly, such excipients can be one or more fillers, binders, colorants, coating agents, slow release compounds, and the like.

In order to produce a flowable mixture which contains the slightly cross-linked rheology modified polymer or copolymers of the present invention as well as the active ingredients, desirably only directly compressible excipients are utilized. Examples of some suitable excipients include microcrystalline cellulose such as Avicel® PH101, Avicel® PH102, Avicel® PH200, Avicel® PH301, and Avicel® PH302 available from FMC Corporation, Vivapur 101 and Virapur 102 available from Rettenmaier and Sohne GMBH , Emcocel 50 M and Emcocel 90 M available from Penwest Company; dicalcium phosphate such as Elcema® available from Degussa; A-Tab®; DiTab® available from Rhodia; lactose monohydrate such as Flow-Lac® 100; Pharmatose®DCL11, Pharmatose®DCL15, Pharmatose®DCL21 available from DMV International; Tablettose® 80 available from Meggle; and tricalcium phosphate such as Tri-Tab®; Fast Flo Lactose from Foremost; and Prosolve® (Silicified MCC) from Penwest.

The amount of the one or more excipients utilized in the directly compressible solid dosage composition is simply the remainder of material required to make a suitable solid dosage form, for example a compressed tablet having a desired amount of active ingredient therein as well as a desirable amount of granulated slightly cross-linked rheology modifying polymer. Hence, the amounts of the excipient can vary widely.

The slightly cross-linked one or more rheology modifying polymers or copolymers, the one or more active ingredients, as well as the one or more excipients are mixed in any conventional manner to produce a blend. For example, it can be mixed in a shell blender, a Vee blender, a double-cone blender, a ribbon mixer, and the like. The mixture containing the granulated slightly cross-linked polymer or copolymer is then directly fed into generally any conventional tablet making machine wherein a desired amount of the mixture or blend is fed through an orifice or opening into a tablet die.

The die is closed and compresses the mixture to produce a suitable sized and shaped solid dosage article such as a tablet. Unexpectedly, use of the granulated slightly cross-linked rheology modifying polymer or copolymer in the mixture of the desirable directly compressible excipient and the active ingredient need not be granulated but, as stated herein above, directly fed into a directly compressing tablet forming machine to form a solid dosage article and the like. That is, the present invention is generally free of any other processing or compounding steps between formation of the mixture or blend comprising the three above noted components and their formation of a solid dosage article.

An important aspect of the present invention is that the granular tableting mixtures have suitable flow properties or flow indices and the same can be readily determined in a manner known to the art and to the literature. For example, the flow index can be measured by Flodex™ equipment, which comprises a 35–45 mm diameter tube approximately 8–10 cm long. Bottom caps with incrementally larger diameter apertures are used in the apparatus until the aperture is found of sufficient diameter that the contents of the tube are substantially emptied from the tube when the aperture is unblocked by the operator. A flow index value is assigned equal to the diameter of the aperture used in mm through which the material flows easily. If the aperture is too small, then bridging over occurs with a substantial amount of the tube contents being retained in the tube. The granular tableting mixtures of the present invention have Flodex™ values of generally 25 or 20 or less, desirably 15 or 10 or less, and preferably 8, 6, 5, or 4 or less, and even 3 or less.

Desirably, the flow characteristics of the compressible granular mixture of the present invention is such that it can flow through at least a hole of the same size or smaller than the die diameter in which the tablet is to be made. In other words, if the tablet diameter is 16 mm, the compressible mixture should be able to flow through at least a 16 mm hole, desirably at least a diameter of 1 mm smaller, i.e. 15 mm, and preferably a diameter of at least 2 mm less, i.e. 14 mm or smaller.

The invention will be better understood by reference to the following examples which serve to illustrate but not to limit the present invention.

In the following examples, R is a rheology modifying polymer or copolymer, E is the excipient and Al is the active ingredient.

EXAMPLE 1

| Ingredients | Source | % w/w | Actual Weight(g) |
|---|---|---|---|
| Acetaminophen (Al) | Spectrum | 20.0 | 30.0 |
| Lactose Monohydrate(E) | Foremost | 20.0 | 30.0 |
| DiTab (E) | Rhone-Poulenc | 20.0 | 30.0 |
| Emcompress (E) | Penwest | 20.0 | 30.0 |
| Granular Carbopol EX507* (R) | BF Goodrich | 20.0 | 30.0 |

| 1.) Add to V-Blender | Grams | |
|---|---|---|
| Acetaminophen | 30.0 | added to V-Blender |
| Lactose Monohydrate | 30.0 | added to V-Blender |
| Emcompress | 30.0 | added to V-Blender |
| Carbopol EX507 | 30.0 | added to V-Blender |
| DiTab | 30.0 | added to V-Blender |

2.) The above formulation was blended for 15 minutes in a Patterson-Kelly Twin Shell Mixer (serial no. B10497).
3.) Placed in 8 oz. jar and tested.

Physical Properties of Formulation:

| | |
|---|---|
| Flodex: | 4 mm |
| Flow Rate: | 9.46 g/sec |
| Bulk Density: | 0.655 g/cc |
| Tap Density: | 0.790 g/cc |
| Hausner Ratio: | 1.206 |
| Compressibility: | 17.09 |
| % Humidity: | 14 |

* EX 507 is Carbopol ® 971 PNF which is manufactured and sold by B.F. Goodrich and is essentially a homopolymer of acrylic acid slightly cross-linked with allyl ether pentaerythritol, which has been granulated in a manner as set forth herein above.

EXAMPLE 2

| Ingredients | Source | % w/w | Actual Weight(g) |
|---|---|---|---|
| Acetaminophen (Al) | Spectrum | 20.0 | 30.0 |
| Lactose Monohydrate(E) | Foremost | 20.0 | 30.0 |
| DiTab (E) | Rhone-Poulenc | 20.0 | 30.0 |
| Emcompress (E) | Penwest | 20.0 | 30.0 |
| Granular Carbopol EX507* (R) | BF Goodrich | 20.0 | 30.0 |

| 1.) Add to V-Blender | Grams | |
|---|---|---|
| Acetaminophen | 30.0 | added to V-Blender |
| Lactose Monohydrate | 30.0 | added to V-Blender |
| Emcompress | 30.0 | added to V-Blender |
| Carbopol EX507 | 30.0 | added to V-Blender |
| DiTab | 30.0 | added to V-Blender |

2.) The above formulation was blended for 15 minutes in a Patterson-Kelly Twin Shell Mixer (serial no. B10497).
3.) Placed in a 8 oz. jar and tested.

Physical Properties of Formulation:

| | |
|---|---|
| Flodex: | 4 mm |
| Flow Rate: | 11.84 g/sec |
| Bulk Density: | 0.668 g/cc |
| Tap Density: | 0.821 g/cc |
| Hausner Ratio: | 1.229 |
| Compressibility: | 18.64 |
| % Humidity: | 20 |

EXAMPLE 3

| Ingredients | Source | % w/w | Actual Weight(g) |
|---|---|---|---|
| Acetaminophen (Al) | Spectrum | 20.0 | 30.0 |
| Lactose Monohydrate(E) | Foremost | 20.0 | 30.0 |
| DiTab (E) | Rhone-Poulenc | 20.0 | 30.0 |
| Emcompress (E) | Penwest | 20.0 | 30.0 |
| Granular Carbopol EX507(R) | BF Goodrich | 20.0 | 30.0 |

| 1.) Add to V-Blender | Grams | |
|---|---|---|
| Acetaminophen | 30.0 | added to V-Blender |
| Lactose Monohydrate | 30.0 | added to V-Blender |
| Emcompress | 30.0 | added to V-Blender |
| Carbopol EX507 | 30.0 | added to V-Blender |
| DiTab | 30.0 | added to V-Blender |

2.) The above experimental formulation was blended for 25 minutes in a Patterson-Kelly Twin Shell Mixer (serial no. B10497).
3.) Placed in a 8 oz. jar and tested.

Physical Properties of Formulation:

| | |
|---|---|
| Flodex: | 4 mm |
| Flow Rate: | 7.19 g/sec |
| Bulk Density: | 0.599 g/cc |
| Tap Density: | 0.731 g/cc |
| Hausner Ratio: | 1.220 |
| Compressibility: | 18.06 |
| % Humidity: | 8 |

As apparent from above, the flow index of the compressible mixture of Examples 1, 2, and 3 which contained a granular rheology modifying polymer was excellent, i.e. readily being able to flow through a 4 mm diameter orifice.

In contrast, Examples 4 and 5 set forth below, which utilized the same granular rheology modifying polymer, did not produce suitable low flow indexes for producing directly compressible mixtures because a directly compressible excipient was not utilized.

EXAMPLE 4

| Ingredients | Source | % w/w | Actual Weight(g) |
|---|---|---|---|
| Crystalline Acetaminophen (Al) | Schweizerhall | 20.0 | 30.0 |
| Crystalline Anhydrous Lactose(E) | Sheffield | 60.0 | 90.0 |
| Granular Carbopol EX507(R) | BF Goodrich | 20.0 | 30.0 |

| 1.) Add to V-Blender | Grams | |
|---|---|---|
| Crystalline Acetaminophen | 30.0 | added to V-Blender |
| Crystalline Anhydrous Lactose | 90.0 | added to V-Blender |
| Granular Carbopol EX507 | 30.0 | added to V-Blender |

2.) The above formulation was blended for 15 minutes in a Patterson-Kelly Twin Shell Mixer (serial no. B10497).
3.) Placed in a 8 oz. jar and tested.

Physical Properties of Formulation:

| | |
|---|---|
| Flodex: | 18 mm |
| Flow Rate: | 0 g/sec |
| Bulk Density: | 0.525 g/cc |
| Tap Density: | 0.708 g/cc |
| Hausner Ratio: | 1.349 |
| Compressibility: | 25.85 |
| % Humidity: | 18 |

EXAMPLE 5

| Ingredients | Source | % w/w | Actual Weight(g) |
|---|---|---|---|
| Crystalline Theophylline (Al) | Ruger | 32.9 | 98.7 |
| Crystalline Anhydrous Lactose (E) | Sheffield | 55.7 | 167.1 |
| Granular Carbopol EX507(R) | BF Goodrich | 10.0 | 30.0 |
| Cab-O-Sil (E) | Cabot | 0.4 | 1.2 |
| Magnesium Stearate (E) | Synpro | 1.0 | 3.0 |

| 1.) Mixed in a mortar & pestle | Grams | |
|---|---|---|
| Cab-O-Sil | 1.2 | milled to a fine powder |
| Theophylline | 48.7 | mixed in with the Cab-O-Sil transferred to V-Blender |

| 2.) Add to V-Blender | Grams | |
|---|---|---|
| Crystalline Theophylline | 50.0 | added to V-Blender |
| Crystalline Anhydrous Lactose | 67.1 | added to V-Blender |
| Crystalline Anhydrous Lactose | 100.0 | added to V-Blender |
| Granular Carbopol EX507 | 30.0 | added to V-Blender |

3.) The above experimental formulation was blended for 25 minutes in a Patterson-Kelly Twin Shell Mixer (serial no. B10497).

4.) Mg. Stearate 3.0 g was added to the formulation and blended for 2 minutes.

5) Divided into 100 gram samples and placed in three 8 oz. jars and tested.

Physical Properties of Formulation:

| | |
|---|---|
| Flodex: | 16 mm |
| Flow Rate: | 3.35 g/sec |
| Bulk Density: | 0.495 g/cc |
| Tap Density: | 0.634 g/cc |
| Hausner Ratio: | 1.281 |
| Compressibility: | 21.92 |
| % Humidity: | 9 |

EXAMPLE 6

| Ingredients | Source | % w/w | Actual Weight(g) |
|---|---|---|---|
| Crystalline Theophylline (Al) | Ruger | 32.9 | |
| Powder Carbopol 971PNF(R) | BF Goodrich | 10.0 | |
| Crystalline Anhydrous Lactose (E) | Sheffield | 55.7 | |
| Cab-O-Sil (E) | Cabot | 0.4 | |
| Magnesium Stearate (E) | Synpro | 1.0 | |
| Total | | 100 | |

Example 6 was prepared in a manner similar to Example 5, that is, Cab-O-Sil and Theophylline were initially mixed in a mortar and pestle and then added to a Vee blender along with additional Crystalline Theophylline, the Crystalline Anhydrous Lactose and the Powder Carbopol and mixed for 25 minutes in a twin shell mixer, and the like. The following physical properties were obtained:

Physical Properties of Formulation:

| | |
|---|---|
| Flodex: | 26 mm |
| Flow Rate: | no flow g/sec |
| Bulk Density: | 0.550 g/cc |
| Tap Density: | 0.753 g/cc |
| Hausner Ratio: | 1.369 |
| Compressibility: | 26.96 |

This Example shows that the use of a non-granulated rheology modifying polymer drastically reduced the flow rate rendering it totally unacceptable for formation of a directly compressed solid article such as a tablet.

The granular mixtures of Examples 1 through 3 were tested in a tablet making machine and produced suitable direct compression tablets. That is, the granular polymer containing mixture per se was compressed and formed in a tablet without any intervening, intermediate, or other steps. Thus, the process for making the compressed tablets simply involves flowing the suitable amount of the granular rheology modifying polymer or copolymer, the active ingredient, and the excipient mixture into a die and compressing the same. The process is thus free of any other steps. The tablets produced by examples 1, 2 and 3 had good controlled released properties. That is the release time of the acetaminophen was 260 minutes when tested using synthetic intestinal fluid in a U. S. P. Type II paddle apparatus.

While in accordance with the Patent Statutes, the best mode and preferred embodiments have been set forth, the scope of the invention is not limited thereto, but rather by the scope of the attached claims.

What is claimed is:

1. A modified release solid dosage article, comprising: a directly compressed blend of at least a) a slightly cross-linked swellable, gel forming granular rheology modifying polymer or copolymer derived from at least one unsaturated carboxylic acid or dicarboxylic acid monomer having a total of from 3 to about 10 carbon atoms, or at least a half ester monomer of said unsaturated dicarboxylic acid with an alkanol having from 1 to about 4 carbon atoms, or combinations thereof, said granular rheology modifying polymer or copolymer containing less than about 5 parts by weight of a monovalent metal cation per 100 parts by weight of said granulated rheology modifying polymer or copolymer, and optionally one or more oxygen containing unsaturated comonomers having from 3 to about 40 carbon atoms, and a cross-linking agent;

b) one or more active ingredients; and c) one or more excipients, said granular rheology modifying polymer or copolymer being capable of swelling to form a viscous gel which retards diffusion of said active ingredient; and wherein said cross-linking agent is an allyl ether of sucrose of pentaerythritol, or a derivative thereof, a polyalcohol, diallylphthalate, divinyl benzene, allyl (meth)acrylate, ethylene glycol di(meth)acrylate, divinylglycol, methylene bisacrylamide, trimethylopropane tri(meth)acrylate, diallyl itaconate, diallyl fumarate, diallyl maleate, a derivative of castor oil, or a polyol esterfied with an ethylenically unsaturated carboxylic acid, or combinations thereof.

2. A modified release solid dosage article according to claim 1, wherein said one or more oxygen containing unsaturated comonomers comprises an anhydride of said unsaturated carboxylic acid, or an alkyl ester of said unsaturated carboxylic acid wherein said alkyl group has from 1 to 30 carbon atoms, or an alkyl vinyl ether wherein said alkyl group has from 1 to about 30 carbon atoms, or an alkyl vinyl ether wherein said alkyl group has from 1 to 20 carbon atoms, or combinations thereof, wherein said slightly cross-linked granulated rheology modifying polymer or copolymer has a particle size from about t40 mesh to about 200 U.S. Standard Mesh, and wherein said excipient is a directly compressible excipient.

3. A modified release solid dosage article according to claim 2, wherein said unsaturated carboxylic acid has from 3 to about 5 carbon atoms, wherein the amount of said one or more oxygen containing comonomers when utilized is from about 0.01 to about 40 percent by weight and wherein the amount of said unsaturated carboxylic acid monomer or said half ester monomer or combinations thereof is from about 60 to about 99.99 percent by weight based upon the total weight of all of said monomers and comonomers, and wherein the amount of said cross-linking agent is from about 0.01 to about 2.0 parts by weight of said monomers and comonomers.

4. A modified release solid dosage article according to claim 3, wherein said slightly cross-linked granulated rheology modifying polymer or copolymer has a particle size of from about 45 to about 150 U.S. Standard Mesh.

5. A modified release solid dosage article according to claim 4, wherein said rheology modifying polymer or copolymer is derived from acrylic acid or maleic acid, or combinations thereof, wherein said cross-linking agent is an allyl ether of sucrose, an allyl ether of pentaerythritol, or diallylphthalate, or combinations thereof, and wherein the amount of said cross-linking agent is from about 0.03 to about 1.0 part by weight per 100 parts by weight of said monomers and comonomers.

6. A modified release solid dosage article according to claim 1, wherein said granulated rheology modifying polymer or copolymer contains less than about 5 parts by weight of water per 100 parts by weight of said granulated rheology modifying polymer or copolymer.

7. A modified release solid dosage article according to claim 3, wherein said granulated rheology modifying polymer or copolymer contains less than about 5 parts by weight of water per 100 parts by weight of said granulated rheology modifying polymer or copolymer.

8. A modified release solid dosage article according to claim 5, wherein said granulated rheology modifying polymer or copolymer contains less than about 2 parts by weight of water per 100 parts by weight of said granulated rheology modifying polymer or copolymer.

9. A control release article comprising the directly compressed solid dosage article of claim 1.

10. A control release article comprising the directly compressed solid dosage article of claim 3.

11. A control release article comprising the directly compressed solid dosage article of claim 5.

12. A directly compressed solid dosage article according to claim 1, wherein said article is a tablet.

13. A directly compressed solid dosage article according to claim 3, wherein said article is a tablet.

14. A directly compressed solid dosage article according to claim 5, wherein said article is a tablet.

* * * * *